United States Patent
Walther et al.

(10) Patent No.: US 6,419,639 B2
(45) Date of Patent: *Jul. 16, 2002

(54) LAPAROSCOPIC SAC HOLDER ASSEMBLY

(75) Inventors: McClellan M. Walther, Gaithersberg; Frank Harrington, Catonsville, both of MD (US)

(73) Assignee: National Institute of Health, Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 30 days.

(21) Appl. No.: 09/368,824

(22) Filed: Aug. 5, 1999

(51) Int. Cl.$^7$ .............................................. B16B 10/00
(52) U.S. Cl. ........................ 600/562; 606/106; 606/174
(58) Field of Search ................................ 600/562, 564; 606/106, 174

(56) References Cited

U.S. PATENT DOCUMENTS

| | | | |
|---|---|---|---|
| 5,215,521 A | * | 6/1993 | Cochran et al. ............... 604/22 |
| 5,312,416 A | * | 5/1994 | Spaeth et al. ................ 606/114 |
| 5,337,754 A | | 8/1994 | Heaven et al. |
| 5,341,815 A | | 8/1994 | Cofone et al. |
| 5,352,184 A | | 10/1994 | Goldberg et al. |
| 5,354,303 A | | 10/1994 | Spaeth et al. |
| 5,368,597 A | | 11/1994 | Pagedas |
| 5,464,403 A | | 11/1995 | Kieturakis et al. |
| 5,647,372 A | | 7/1997 | Tovey et al. |
| 5,720,754 A | | 2/1998 | Middleman et al. |

FOREIGN PATENT DOCUMENTS

| | | |
|---|---|---|
| DE | 25796 | 1/1984 |
| EP | 0 446 020 A1 | 9/1991 |

OTHER PUBLICATIONS

Rassweiler et al., "Organ Retrieval Systems for Endoscopic Nephrectomy: A Comparative Study", Journal of Endourology, vol. 12, No. 4, Aug. 1998.

* cited by examiner

*Primary Examiner*—Cary O'Connor
*Assistant Examiner*—Pamela Wingood
(74) *Attorney, Agent, or Firm*—Knobbe, Martens, Olson & Bear, LLP (57) ABSTRACT

This invention relates to a surgical device and methods for accessing and retrieving a tissue mass from a body cavity through a minimally invasive laparoscopic procedure. The device consists of a handle comprising an inner rod, which is rotatably engaged within a tubular member, and a loop adapted to hold a surgical bag. The loop comprises first and second bowed leaf elements, wherein the first bowed leaf element is attached to the inner rod and the second bowed leaf element is attached to the tubular member. The device further has a rotatable articulation, such as a hinge, joining the first and second bowed leaf elements, wherein rotation of the inner rod causes the first bowed leaf element to rotate about the articulation, such that the surgical bag may be opened and closed by rotation of the inner rod.

14 Claims, 3 Drawing Sheets

LAPAROSCOPIC SAC HOLDER ASSEMBLY

BACKGROUND OF THE INVENTION

1. Field of the Invention

This invention relates to a surgical device and methods for accessing and retrieving tissue from a body cavity through minimally invasive endoscopic procedures.

2. Description of the Related Art

In recent years, the applications for endoscopic surgery, and in particular, laparoscopic surgery, have expanded to include many different procedures. A benefit of laparoscopic operations is the relatively quick recovery period experienced by patients, due to the small incisions that are made in the body. These incisions reduce the trauma and the required healing compared to traditional surgery. Laparoscopic tubes and sleeves with diameters on the order of about 5 to 15 millimeters are inserted through the incisions to aid in accessing the tissue in the body cavity. Various instruments and video camera are typically directed through the laparoscopic sleeves for performing and monitoring the surgical steps.

A particular concern in laparoscopic surgery is the transporting of tissues and other mass that are cut away or retrieved during the surgery. While moving, manipulating or morcellating the mass within the body cavity, pieces of infected or cancerous mass, blood, bile, and other liquids may escape and pose infection problems or other complications. It is desirable to contain these materials in a bag or similar enclosure within the body cavity before removal to minimize the risk of infection or other complications. Thus, while it is important that the bag possess sufficient stability and impermeability, particularly during mechanical morcellation, it is also desirable that containment of the materials be accomplished as quickly as possible with minimal disturbance to the surgical site.

Instruments with bags have been designed in an attempt to avoid the complications associated with the removal of tissue during laparoscopic surgery. These devices have provided a bag supported by a loop on the end of a handle, wherein the handle provides a means for opening the bag inside the body cavity to receive the tissue. The opening means typically relies on the springiness or shape memory of the loop material upon release from a radially restrained configuration. Prior art devices also employ a means to close the bag before withdrawing the tissue from the body cavity. The closing means usually involve a drawstring mechanism.

One such device is disclosed by Tovey et al. in U.S. Pat. No. 5,647,372, wherein the specimen retrieval device consists of a handle with a loop at the distal end for supporting the mouth of a specimen bag. The device is introduced into the patient's body cavity in a sheath. The loop is formed from two bowed spring strips made of elastic metal or plastic. The proximal ends of the two spring strips are attached to an inner "drive rod" in the handle, the bowed regions extending in opposite directions to define a loop. The loop with attached bag is deployed by distally advancing the drive rod out of the sheath. The spring strips bow outward defining a loop and opening the mouth of the bag. After the specimen is deposited in the bag, a drawstring is pulled to close the bag.

Similarly, Middleman et al., U.S. Pat. No. 5,720,754, discloses a device having an elongate handle with an elastic loop made of spring metal or memory alloy at the distal end of the handle. The handle consists of an outer sheath and a slideably engaged inner rod. The loop is attached to the inner rod and may be deployed by distally advancing the inner rod within the sheath and removed by proximally retracting the inner rod within the sheath. In one embodiment, the loop that supports the bag includes two curved, spring metal arms within the neck of the bag; the arms do not join one another. Middleman, like Tovey, also employs a drawstring mechanism for closing the bag.

Heaven et al., U.S. Pat. No. 5,337,754 describes another isolation bag, which can be inserted into a body cavity through a tube in its collapsed configuration and then inflated by application of gas or liquid to its expanded configuration. In addition, the bag wall can include wires, such as shape memory alloy, that will assist the bag in opening and maintaining its open configuration. Similarly, Cofone et al., U.S. Pat. No. 5,341,815, describes a pouch having a shape memory metal loop for opening the pouch. The devices disclosed by both Heaven and Cofone include a drawstring for closing the bag.

There remains a need for a device adapted to easily open and close a sac designed for receiving large tissue masses. None of the prior art devices disclose a loop formed by two bowed leaf elements joined by a hinge, wherein the loop can be easily opened and closed by rotating one leaf about the hinge with respect to the other leaf.

SUMMARY OF THE INVENTION

A surgical device for holding a sac for laparoscopic surgery is disclosed in accordance with the present invention. The device consists of rotatable hinge joining first and second bowed leaf elements. The bowed leaf elements form a loop which is adapted to open and close the sac by rotation of the bowed leaf elements.

In one embodiment, the surgical device also comprises an inner rod. The first bowed leaf element is attached to the distal end of the inner rod. In a further variation, the device also has a tubular member. The second bowed leaf element is attached to a distal end of the tubular member. In a further variation, the inner rod is rotatably engaged in the tubular member. Preferably, a user rotatable knob is attached to the proximal end of the inner rod, such that rotating the knob causes the first bowed leaf element to rotate with respect to the second bowed leaf element. In one embodiment, the surgical device includes a surgical sac. The sac preferably has a neck region with a drawstring.

In a variation, a laparoscopic sac holder assembly for inserting a surgical bag into a body cavity is disclosed. The assembly has of a handle comprising an inner rod, a tubular member and an outer sheath, wherein the inner rod is rotatably engaged within the tubular member, which is slideably engaged within the outer sheath. The assembly also includes a loop member comprising first and second bowed leaf elements, the first bowed leaf element being attached to the inner rod and the second bowed leaf element being attached to the tubular member, wherein the surgical bag is attached to the loop member. The first and second bowed leaf elements are joined by a rotatable articulation.

The assembly preferably includes a means for rotating the inner rod, wherein rotation of the inner rod causes the first bowed leaf element to rotate about the rotatable articulation relative to the second bowed leaf element, such that the loop member is rotatably adjustable between at least a first closed configuration and a second open configuration. The surgical bag employed in the laparoscopic sac holder assembly of the present invention may have a neck region with a drawstring. Further, the surgical bag may be adapted to be removed from the loop member within the body cavity.

Also disclosed is a method of performing a laparoscopic surgical procedure. The method comprises providing a laparoscopic sac holder assembly having a surgical bag with a mouth portion attached to a hinged loop member, said hinged loop member being rotatably adjustable between a first closed position and a second open position, wherein said hinged loop member is in the first closed position, such that the mouth portion of the attached surgical bag is closed. The laparoscopic sac holder assembly is inserted into a body cavity. The hinged loop member is rotatably adjusted to the second open position, such that the mouth portion of the attached surgical bag is opened. An excised tissue mass is placed within the open surgical bag.

In a variation of the method, a tissue morcellation device is inserted into the open surgical bag containing the tissue mass and the tissue mass is morcellated. In a further variation, prior to inserting the morcellation device into the surgical bag, the surgical bag is detached from the hinged loop member. The mouth portion of the detached surgical bag may be withdrawn to a position outside of the body cavity before morcellating the tissue mass.

A method of making a laparoscopic sac holder in accordance with the present invention is also disclosed. The method consists of the steps of providing a handle having an inner rod, rotatably engaged in a tubular member, attaching a first bowed leaf element to the inner rod, attaching a second bowed leaf element to the tubular member, and joining the first and second bowed leaf elements by a rotatable articulation.

DETAILED DESCRIPTION OF THE PREFERRED EMBODIMENT

As defined in this application, the word "distal" is used, conventionally, to describe that portion of the device which extends away from the user during use, and the word "proximal" is used, conventionally, to describe that portion of the device that extends toward the user during use.

The term "laparoscopic sac holder" is used herein to encompass any device used for introducing a bag or sac via laparoscopic or other minimally invasive surgical procedures into a body cavity for isolating and/or retrieving a tissue mass. The mechanical disruption, or "morcellation" of the tissue mass is frequently desirable during laparoscopic procedures in order to facilitate withdrawal and/or aspiration of the tissue through a relatively small port. However, it is not a required feature of the present invention that it be used only in surgical procedures that involve tissue morcellation.

Further, the terms "sac", "bag" and "pouch" are used interchangeably herein.

Figure 1:
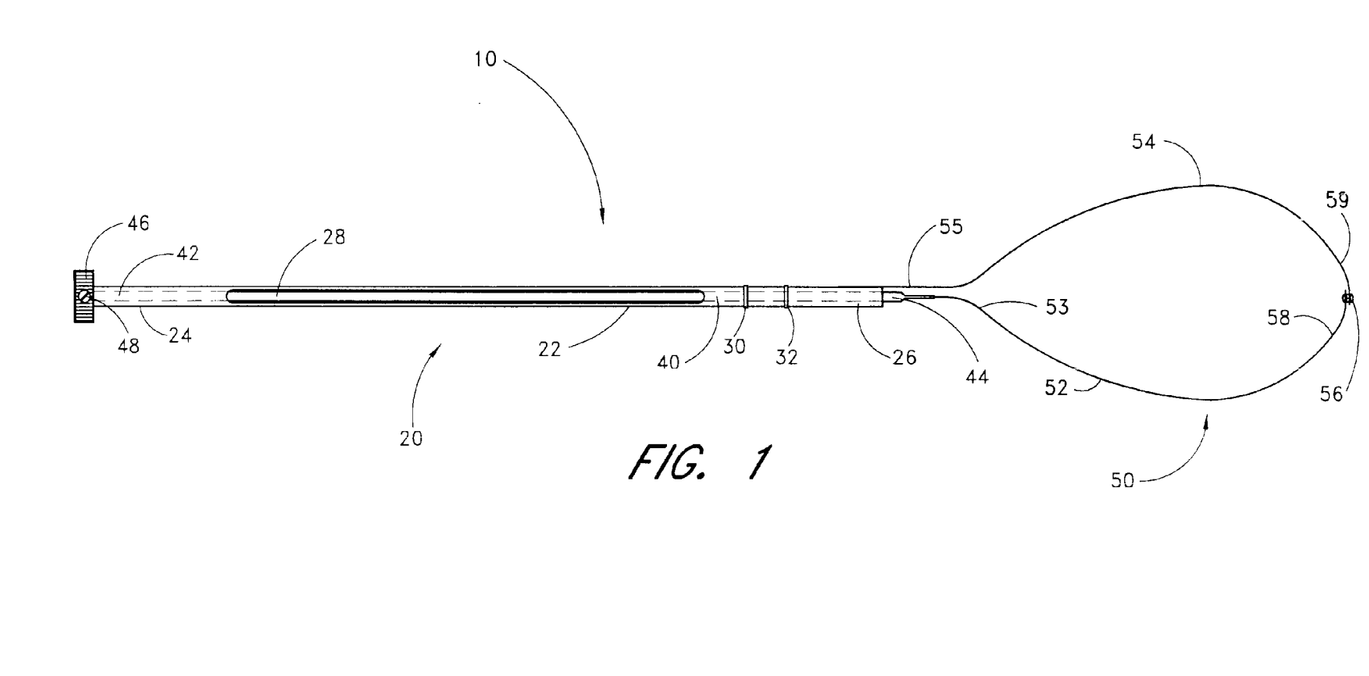
FIG. 1 is a perspective view of a laparoscopic sac holder in accordance with the present invention showing a hinged loop comprising two bowed leaf elements, one attached to a tubular member and the other attached to a rotatable inner rod.

Referring to FIG. 1, a laparoscopic sac holder 10 in accordance with one embodiment of the present invention is illustrated. The laparoscopic sac holder 10 includes a handle 20 having a loop member 50 disposed at the distal end. The handle further comprises a tubular member 22 with proximal 24 and distal 26 end portions. In a preferred variation of the laparoscopic sac holder 10, the tubular member 22 has a notch 28 that runs in a longitudinal axis along a portion of the length of the tubular member 22. As will become apparent with reference to FIG. 2, the notch 28 is adapted to serve as a guide for the longitudinal sliding of the tubular member 22 in relation to an outer sheath 60 during the introduction, deployment and retraction of the laparoscopic sac holder 10 from the body cavity. The structure and function of the notch 28 is described in greater detail below with reference to FIG. 2. The tubular member 22 is also shown having proximal 30 and distal 32 O-rings, which provide a sealing means between the tubular member 22 and the outer sheath 60 (not shown in FIG. 1) to minimize the escape and/or entry of gases into the body cavity during the operation.

An inner rod 40, depicted in phantom, is rotatably engaged within the tubular member 22. The rotatable inner rod 40 has proximal 42 and distal 44 end portions. The proximal end portion 42 extends proximally beyond the proximal end portion 24 of the tubular member 22, whereupon a knob 46 is attached to the proximal end portion 42 of the inner rod 40 by means of a setscrew 48. When the setscrew 48 of the knob 46 is tightened to engage the inner rod 40, manual rotation of knob 46 causes the inner rod 40 to rotate within the tubular member 22. Other means, both "permanent" and "removable", for fastening the knob or equivalent user operable structure to the inner rod will be appreciated by those of skill in the art. Such other means may include pin, solder, epoxy, weld, threading, etc.

Equivalent user operable structure for use in rotating the inner rod may include, for example, a rod-shaped handle perpendicular to the longitudinal axis of the device, a lever, a faucet-type fitting, etc. Motorized means for rotating the inner rod are also encompassed within the present disclosure. For example, the inner rod may be rotated by electric, pneumatic or fluid drive system, or any other motor used in the art to generate rotation. The rotating drive means may be automated to allow precise control of opening and closing operations, e.g., to produce a 180° rotation.

The distal end portion 44 of the inner rod 40 extends distally beyond the distal end portion 26 of the tubular member 22. The distal end portion 44 is adapted to fastenably engage the proximal end 53 of the first bowed leaf element 52 of the loop member 50. Suitable fastening means are well known in the art and include screws, rivets, bolts and nuts, solder, weld, crimped ferrule, etc., and combinations thereof. In a variation, the inner rod 40 and first bowed leaf element 52 may be a continuous, monolithic structure, which is constructed to have the form of a cylinder-shaped rod inside the tubular member 22 and a ribbon-shaped bowed leaf within the loop member 50. The proximal end 55 of the second bowed leaf element 54 is attached by conventional means (see above) to the distal end portion 26 of the tubular member 22. The first 52 and second 54 bowed leaf elements are joined at their distal ends 58,59 by a rotatable articulation 56, such as a hinge, pin, rivet, joint, screw, etc.

As a result of the rotatable articulation 56, and the attachment of the first bowed leaf element 52 to the rotatable inner rod 40, and the attachment of the second bowed leaf element 54 to the fixed tubular member 22, as detailed above, the loop member may assume an open configuration, as illustrated in FIG. 1, wherein the leaves 52,54 are bowed apart and 180° opposed. When the inner rod 40 is manually rotated by 180° using the knob 46, the loop member 50 assumes a closed configuration, wherein the leaves 52,54 are nested together and bowed in the same direction.

Figure 2:
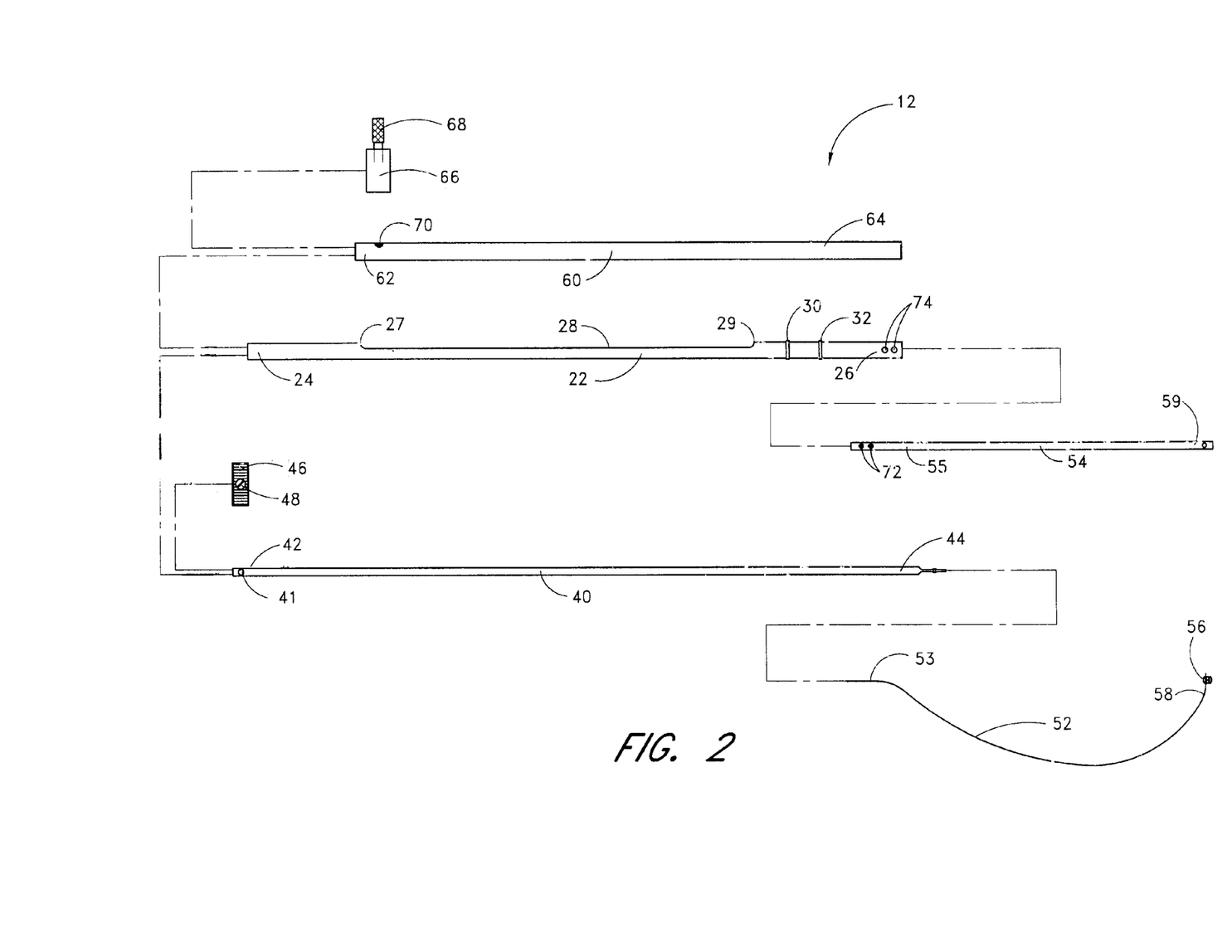
FIG. 2 is an exploded plan view of an embodiment of the laparoscopic sac holder assembly of the present invention showing a rotatable inner rod with first bowed leaf element and operating knob, a tubular member with second bowed leaf element, and an outer sheath with retainer ring.

Referring to FIG. 2, there is shown an exploded view of the laparoscopic sac holder assembly 12 of the present invention. Construction of the assembly 12 can best be understood by reference to this drawing. The proximal end 53 of the first bowed leaf element 52 is attached to the distal end 44 of the rotatable inner rod 40. Attachment means are discussed above. The inner rod 40 is rotatably engaged within tubular member 22. Knob 46 is attached and secured to the proximal end portion 42 of the inner rod 40, by tightening setscrew 48, or other means as detailed above. A receiving aperture 41, which may or may not be threaded, may be included along the proximal end portion 42 of the inner rod 40 in order to provide a positive transfer of rotational torque from the knob 46 to the inner rod 40.

The proximal end 55 of the second bowed leaf element 54 is attached to the distal end 26 of the tubular member 22. Attachment may be made by any means known in the art as discussed above, including screws, bolts and nuts, rivets, welds, solders, epoxy, etc. In the embodiment illustrated in FIG. 2, attachment means 72 (e.g., screws, rivets, etc.) on the distal end 55 of the second bowed leaf element 54 are shown aligned with receiving holes 74 in the distal end 26 of tubular member 22. Because the tubular member 22 sealably slides within outer sheath 60 and rotatably engages inner rod 40, it is desirable that the attachment means 72 exhibit a low inner and outer profile. Recessed sockets for screws, nuts and/or bolts may be employed to ensure low profile. Alternatively, the second bowed leaf element 54 may be continuous and monolithic with the tubular member 22, as discussed above with respect to the first bowed leaf element 52 and the inner rod 40.

Tubular member 22 is further shown to have two O-rings 30,32 that provide a sealing means between tubular member 22 and outer sheath 60. Other sealing means consistent with the present invention include a coating of viscous silicon or other grease between the tubular member and the outer sheath. Moreover, a sufficiently gas-tight seal may be formed in part by the close tolerance employed between the tubular member 22 and the outer sheath 60, particularly where the tubular member is fabricated from or coated with a lubricious polymeric material. Any combination of known sealing means may be employed in the construction and operation of the present invention. Sealing may be important in laparoscopic procedures, particularly when the body cavity is insufflated with pressurized gas to expand the operating clearance.

When fully assembled, inner rod 40, tubular member 22 and outer sheath 60 are coaxially arranged. Retainer ring 66 slides over the outer sheath 60 and is aligned over aperture 70 in the proximal end portion 62 of the outer sheath 60. The retainer ring 66 has a user operable setscrew 68, which when tightened, extends through aperture 70 and into the underlying longitudinal notch 28 in tubular member 22. The engagement of the retainer ring set screw 68 in notch 28 limits the longitudinal travel distance of the outer sheath 60 with respect to tubular member 22. When the outer sheath 60 is positioned as far distally as possible with respect to tubular member 22, i.e., the retainer ring set screw 68 contacts the distal end 29 of notch 28, the outer sheath 60 covers the bowed leaf elements 52,54 in their closed state, for insertion into and withdrawal from the body cavity. Conversely, when the outer sheath 60 is positioned as far proximally as possible with respect to tubular member 22, i.e., the retainer ring set screw 68 contacts the proximal end 27 of notch 28, the bowed leaf elements 52,54 are exposed and may be opened and closed by rotation of knob 46. The engagement of the retainer ring set screw 68 in notch 28 also prevents rotational movement of the outer sheath 60 and tubular member 22 with respect to one another.

Figure 3:
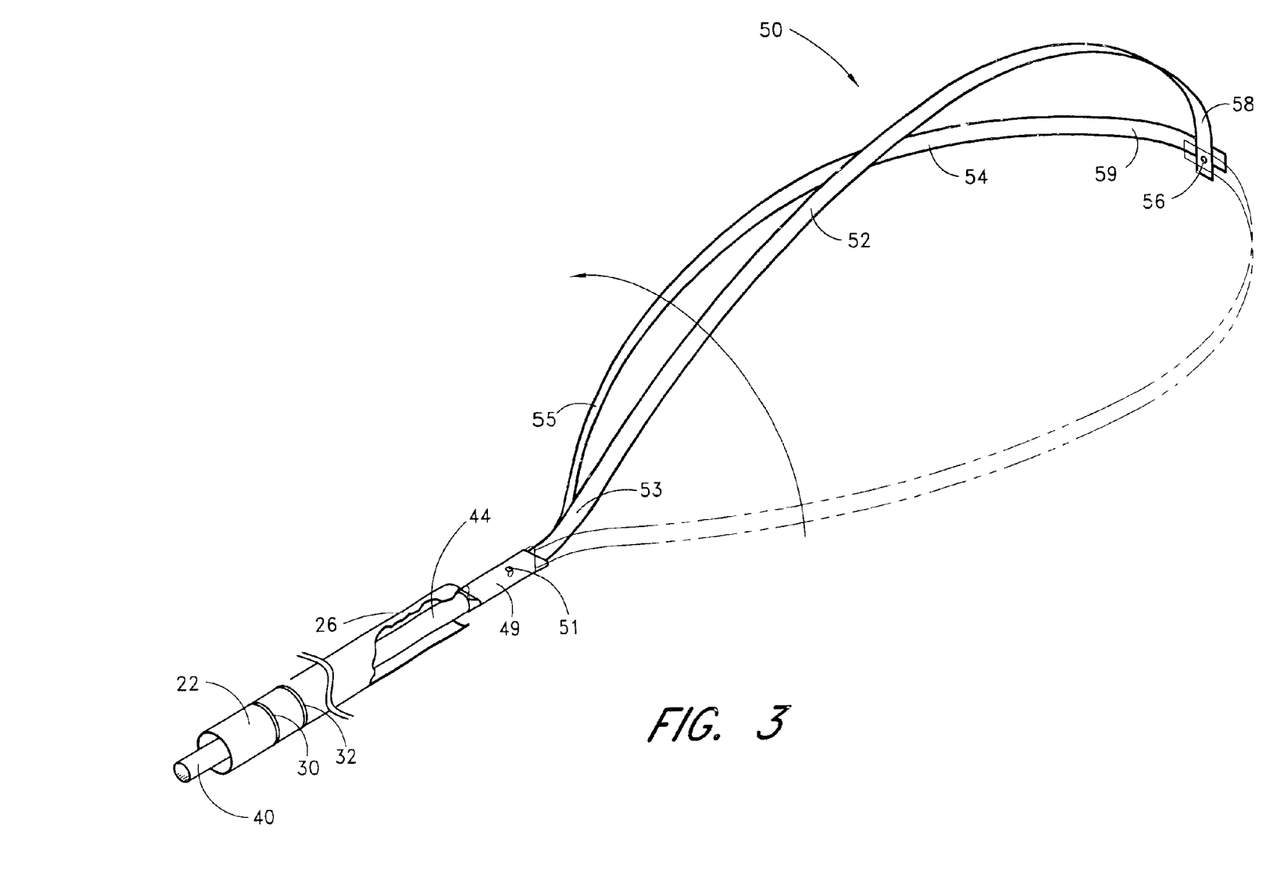
FIG. 3 is an enlarged perspective view of the distal end of a laparoscopic sac holder of the present invention with a section of the tubular member broken away to illustrate rotation of a first bowed leaf element attached to a rotatable inner rod in relation to a second bowed leaf element attached to the tubular member.

Referring to FIG. 3, there is shown an enlarged perspective view of the distal end of an embodiment of the laparoscopic sac holder 10 of the present invention with a section of the distal end portion 26 of tubular member 22 broken away. O-rings 30,32 are shown near the distal end portion 26 of tubular member 22. The proximal end 55 of the second bowed leaf element 54 is attached to the distal end portion 26 of the tubular member 22, as discussed above with any suitable low-profile fastening means. As a consequence, the rotational orientation of the second bowed leaf element 54 is fixed with respect to the tubular member 22.

The proximal end 53 of the first bowed leaf element 52 is attached to the distal end portion 44 of the inner rod 40. One attachment means 51, e.g., screw, rivet, etc., is shown. However, any number and variety of different attachment means and combinations thereof may be used as detailed above. Moreover, since the rotational torque of the inner rod is transferred to the first bowed leaf member, the attachment means preferably provides a positive transfer of this torque. Accordingly, in the embodiment shown in FIG. 3, the distal end 44 of the inner rod 40 is modified to include a flattened ferrule 49 for receiving the ribbon-shaped leaf element 52.

The first 52 and second 54 bowed leaf elements are joined at their distal ends by a rotatable articulation 56, e.g., a hinge, pin or rivet. The articulation allows the first bowed leaf element 52 to rotate, as indicated by the arrow, relative to the second bowed leaf element 54, which is fixed to the tubular member 22. Thus, the loop 50 can adopt a closed configuration, wherein the first bowed leaf element 52 is nested within the arc of the second bowed leaf element 54, and an open configuration, wherein the two leaf elements are bowed in opposite directions, as shown in phantom. The user can easily actuate the change from closed to open configurations by rotating the knob 46 (not shown in FIG. 3) attached to the proximal end of the inner rod 40.

Commercially available surgical bags or sacs may be used in accordance with the present invention, including bags with a drawstring around the mouth of the bag. The bags are preferably attached to the loop during assembly. Indeed, in a preferred embodiment of the present invention, the laparoscopic sac holder assembly with the sac is provided intact as a sterile disposable unit. In a variation, the laparoscopic sac holder assembly may be reused by attaching a new sac to the loop and sterilizing the assembly. In any case, attachment of a bag to the loop may be accomplished by suturing the mouth of the bag to the bowed leaf elements. Alternatively, the bowed leaf elements may be passed through a channel in the neck of the bag prior to forming the rotatable articulation between the bowed leaf elements, or prior to fastening the proximal end(s) of the bowed leaf element(s) to the handle. In a variation, the bag may be secured to the intact loop by folding the upper portion of the open end of the bag over the loop and about itself to form a flap and then sealing the folded-over flap to the bag to create a channel. Sealing can be accomplished by conventional means including heat sealing, ultrasonic welding and the like.

The sac may be constructed of a wide variety of materials, but generally a biocompatible and non-toxic material is preferred. In addition, the material preferably exhibits sufficient conformability to fit within the outer sheath. It is also desirable that the bag be waterproof and exhibit a high tear or burst resistance to prevent fluids, tissue and fragments of tissue from escaping. Physical integrity of the bag is particularly important in applications where the tissue mass is subjected to mechanical morcellation prior to removal from the body cavity.

Suitable materials for construction of the bag include polymeric materials, such as but not limited to PVC, PVC copolymers, chlorinated polyethylene, ethylene ethyl acrylate copolymers, butadiene styrene block copolymers, polyethylene terephthalate, ionomers, polyisoprene, silicones, polyethylene, polyethylene copolymers, ethylene vinyl acetate copolymers, fluoropolymers, polyvinylidene fluoride, polypropylene, polypropylene copolymers, nylons, polyurethanes, PEBAX® block copolyetheramide, PLATILON®, MEDIFILM®, polyamid, and other suitable polymers, blends and mixtures thereof. In some embodiments of this device where very high strength is desired, the bag may be constructed from a fiber or cloth reinforced polymer, such as polyethylene polyester fabric or nylon fabric composites, natural rubber polyester fabric or nylon fabric composites, fabrics such as GORETEX®, and composites and laminates of suitable materials, as will be apparent to those skilled in the art.

The inner rod may be made from any material that exhibits sufficient torsional strength to permit positive transfer of the rotational torque imparted by the user via the knob at the proximal end to the first bowed leaf element at the distal end. Preferably, the inner rod is made from a metallic alloy, such as stainless steel, or polymeric material. Likewise, the outer sheath may be made from a metallic alloy, such as stainless steel, or polymeric material. In any case, the material should be non-toxic and compatible with introduction into the body cavity.

The tubular member may also be made from a metallic alloy, such as stainless steel, or polymeric material. Preferably, the tubular member is made from a suitable polymeric material, such as but not limited to PVC, polypropylene, polyethylene, polyimide, polystyrene, and the like, as well as blends and mixtures thereof, known in the art. In one embodiment, the tubular member may be constructed from a metallic alloy such as stainless steel, coated with a polymer having a relatively low coefficient of friction, as will be apparent to those skilled in the art. A polymeric surface of the tubular member may facilitate sliding of the tubular member with respect to the outer sheath and rotation of the inner rod within the tubular member.

The bowed leaf elements are made from any material known in the art, having sufficient strength, springiness and shape memory, including metallic alloys, such as spring steel and stainless steel, and polymeric materials. Polymer-coated metallic alloys may also be employed. Preferably, the bowed leaf elements are made from a material that is biocompatible and rust-resistant.

The outer diameter of the complete assembly, i.e., the diameter of the outer sheath, is preferably in a range of about 5 to about 20 millimeters, and more preferably about 10 millimeters.

Laparoscopic and other minimally invasive surgical procedures usually require placement of at least one trocar assembly through a body wall to provide access to the body cavity for the surgical instruments. The trocar assembly may include an obturator with a sharp, tissue piercing point, a cannula having a tube and a proximal section that usually includes valve and sealing means. Conventional trocar assemblies may be used in accordance with the present invention. The surgeon inserts the trocar assembly into the body wall and then removes the obturator leaving the cannula inserted into the body cavity and the proximal section outside the body. The body cavity is then insufflated, usually with $CO_2$. Additional cannulas can be inserted and various operating and optical viewing instruments may be inserted through the several cannulas, as will be appreciated by those of skill in the art. The cannula sealing means helps prevent the escape or entry of gas between the inside of the cannula and the outside of the instrument. The instruments, including the laparoscopic sac holder assembly of the present invention, generally have internal sealing means, such as the O-rings on the tubular member, to prevent the escape or entry of gas through the interior of the instrument. Placement of trocar cannulas and insertion of instruments therethrough are performed in accordance with methods and apparatus known and commonly available to those with skill in the art.

The laparoscopic sac holder assembly of the present invention is introduced into a body cavity through a cannulated access port (installed as described above; not shown). The loop and the mouth of the pre-loaded bag are in their closed configurations, wherein the two leaf elements are nested together and restrained in a substantially linear state within the outer sheath, which is in its distal-most position. Once inside the body cavity, the surgeon can deploy the leaf elements and attached bag by retracting the outer sheath relative to the underlying tubular member. The leaf elements, which are nested in their closed configuration, spring to their bowed state by virtue of the springiness of the leaf material. At the appropriate time, the surgeon may open the bag by rotating by 180° the knob attached to the proximal end of the inner rod. Consequently, the first bowed leaf element, attached to the inner rod rotates about the hinge relative to the second bowed leaf element, whereupon, the mouth of the bag is held open by the oppositely bowed leaf elements.

After the surgeon has placed the excised tissue mass in the bag using conventional laparoscopic instruments via additional access port(s), the bag may be closed by rotating the knob 180°, re-sheathed, and withdrawal from the body cavity through the access port. It is also a feature of the present invention, that the bag containing the excised tissue may be closed by rotating the knob 180°, in order to isolate the potentially hazardous tissue from the body cavity, and subsequently, reopened to receive additional tissue. The ability to repetitively open and close the bag, which is made possible by the hinged design of the loop member, is not possible with conventional drawstring devices.

In one preferred variation of the method of using the present invention, where the size of the tissue mass is too large to remove intact via the access port, the tissue may be broken into tiny fragments and/or partially liquefied using a conventional tissue morcellation instrument. The morcellation device may be inserted via a second access port into the bag containing the tissue mass and actuated from outside of the patient.

After morcellation, the dispersed tissue mass may be removed by aspiration from the second access port, or other standard procedure. In this case, the mouth of the bag may be left in an open or partially open configuration during morcellation. Alternatively, where the volume of morcellated tissue is sufficiently small, the bag may be closed and the tissue withdrawn together with the laparoscopic sac holder.

In a variation of the above method for using the invention to isolate and retrieve a large tissue mass, e.g., a kidney, the attached bag is fitted with a conventional drawstring. The excised tissue mass is placed in the open bag as above. Then the bag is removed from the loop while still inside the body cavity by cutting the sutures that attach the bag to the loop or by tearing along a preformed perforation. The drawstring surrounding the mouth of the bag is then grasped by a suitable instrument from a second access port or incision and pulled out of the body cavity, such that the substantially closed mouth and neck of the bag emerges from the body cavity. A morcellation device can then be inserted through the mouth and neck of the bag, into the portion of the bag remaining within the body cavity, which holds the excised tissue. The tissue is then morcellated and may be removed by aspiration and/or pulled out of the body cavity through the second access port or incision, as will be appreciated by those of skill in the art.

While we have described a number of embodiments of this invention, it is apparent that our description of the invention can be altered to provide other embodiments that utilize the basic methods and compositions of this invention. Therefore, it will be appreciated by those of skill in the art that the scope of this invention is to be defined by the claims appended hereto rather than the specific embodiments that have been described in detail above by way of example.

What is claimed is:

1. A surgical device for holding a sac comprising a rotatable hinge joining first and second bowed leaf elements, said bowed leaf elements forming a loop adapted to open and close the sac by rotation of said bowed leaf elements, an inner rod having proximal and distal ends, wherein said first bowed leaf element is attached to the distal end of said inner rod, and a tubular member having proximal and distal ends, wherein said second bowed leaf element is attached to the distal end of said tubular member.

2. The surgical device of claim 1, wherein said inner rod is rotatably engaged in said tubular member.

3. The surgical device of claim 2, wherein a user rotatable knob is attached to the proximal end of said inner rod, such that rotation of the knob causes the inner rod with attached first bowed leaf element to rotate with respect to the tubular member with attached second bowed leaf element.

4. The surgical device of claim 1, wherein the sac is attached to said loop.

5. The surgical device for holding a sac, the device having a rotatable hinge joining first and second bowed leaf elements, said bowed leaf elements forming a loop adapted to open and close the sac by rotation of said bowed leaf elements, wherein the sac is attached to said loop and wherein the sac has a neck region with a drawstring.

6. A device for holding a sac for laparoscopic surgery, comprising:
    a handle comprising an inner rod which is rotatably engaged within a tubular member;
    a loop adapted to hold the sac, the loop comprising first and second bowed leaf elements, wherein the first bowed leaf element is attached to the inner rod and the second bowed leaf element is attached to the tubular member; and
    a rotatable hinge joining the first and second bowed leaf elements, wherein rotation of the inner rod causes the first bowed leaf element to rotate about the hinge, such that the sac may be opened and closed by rotation of the inner rod.

7. A laparoscopic sac holder assembly for inserting a surgical bag into a body cavity, comprising:
    a handle comprising an inner rod, a tubular member and an outer sheath, wherein the inner rod is rotatably engaged within the tubular member which is slideably engaged within the outer sheath;
    a loop member comprising first and second bowed leaf elements, the first bowed leaf element being attached to the inner rod and the second bowed leaf element being attached to the tubular member, and said surgical bag attached to said loop member; and
    a rotatable hinge joining the first and second bowed leaf elements.

8. The laparoscopic sac holder assembly of claim 7, further comprising a means for rotating the inner rod, wherein rotation of the inner rod causes the first bowed leaf element to rotate about the rotatable hinge relative to the second bowed leaf element, such that the loop member is rotatably adjustable between at least a first closed configuration and a second open configuration.

9. The laparoscopic sac holder assembly for inserting a surgical bag into a body cavity, comprising:
    a handle comprising an inner rod, a tubular member and an outer sheath, wherein the inner rod is rotatably engaged within the tubular member which is slideably engaged within the outer sheath;
    a loop member comprising first and second bowed leaf elements, the first bowed leaf element being attached to the inner rod and the second bowed leaf element being attached to the tubular member, wherein said surgical bag is attached to said loop member, and wherein said surgical bag has a neck region with a drawstring and wherein said surgical bag is adapted to be removed from said loop member within the body cavity; and
    a rotatable hinge joining the first and second bowed leaf element.

10. A method of performing a laparoscopic surgical procedure, comprising:
    providing a laparoscopic sac holder assembly having a surgical bag with a mouth portion attached to a hinged loop member comprising first and second bowed leaf elements, a handle comprising an inner rod and a tubular member, the first bowed leaf element being attached to the inner rod and the second bowed leaf element being attached to the tubular member, said hinged loop member being rotatably adjustable between a first closed position and a second open position, wherein said hinged loop member is in the first closed position, such that the mouth portion of the attached surgical bag is closed;
    inserting the laparoscopic sac holder assembly into a body cavity;
    rotatably adjusting said hinged loop member to the second open position, such that the mouth portion of the attached surgical bag is opened; and
    placing an excised tissue mass within the open surgical bag.

11. The method of claim 10, further comprising the steps of inserting a tissue morcellation device into the open surgical bag containing the tissue mass and morcellating the tissue mass.

12. A method of performing a laparoscopic surgical procedure, comprising:
    providing a laparoscopic sac holder assembly having a surgical bag with a mouth portion attached to a hinged loop member comprising first and second bowed leaf elements, a handle comprising an inner rod and a tubular member, the first bowed leaf element being attached to the inner rod and the second bowed leaf element being attached to the tubular member, said hinged loop member being rotatably adjustable between a first closed position and a second open position, wherein said hinged loop member is in the first closed position, such that the mouth portion of the attached surgical bag is closed;

inserting the laparoscopic sac holder assembly into a body cavity;

rotatably adjusting said hinged loop member to the second open position, such that the mouth portion of the attached surgical bag is opened; and placing an excised tissue mass within the open surgical bag.

13. The method of claim 12, wherein after the bag is detached from the hinged loop member, but before the morcellation device is inserted into the bag, the mouth portion of the detached surgical bag is withdrawn to a position outside of the body cavity.

14. A method of making a laparoscopic sac holder comprising:

providing a handle having an inner rod, rotatably engaged in a tubular member;

attaching a first bowed leaf element to the inner rod;

attaching a second bowed leaf element to the tubular member; and joining the first and second bowed leaf elements by a rotatable articulation.

* * * * *

UNITED STATES PATENT AND TRADEMARK OFFICE
CERTIFICATE OF CORRECTION

PATENT NO.   : 6,419,639 B2
DATED        : July 16, 2002
INVENTOR(S)  : McClellan M. Walther and Frank Harrington It is certified that error appears in the above-identified patent and that said Letters Patent is hereby corrected as shown below:

Column 9,
Line 47, the first word "The" should be changed to -- A --.

Column 10,
Line 10, after "...tubular member," the word "and" should be changed to -- wherein --.
Line 36, the last word "element" should be changed to -- elements --.

Column 11,
Lines 1-5, the phrase "comprising first and second bowed leaf elements, a handle comprising an inner rod and a tubular member, the first bowed leaf element being attached to the inner rod and the second bowed leaf element being attached to the tubular member" should be deleted.
Line 9, the word "porition" should be changed to -- portion --.
Line 17, a semicolon should replace the period after "bag", and the following limitations should be added to the Claim:
-- detaching the surgical bag from the hinged loop member;
inserting a tissue morcellation device into the open surgical bag containing the tissue mass; and morcellating the tissue mass. --

Signed and Sealed this

First Day of July, 2003

JAMES E. ROGAN
*Director of the United States Patent and Trademark Office*